United States Patent
Peterson

(10) Patent No.: US 10,083,496 B2
(45) Date of Patent: *Sep. 25, 2018

(54) MACHINE VISION SYSTEMS AND METHODS WITH PREDICTIVE MOTION CONTROL

(71) Applicant: COGNEX CORPORATION, Natick, MA (US)

(72) Inventor: Dale Peterson, Waukesha, WI (US)

(73) Assignee: Cognex Corporation, Natick, MA (US)

(*) Notice: Subject to any disclaimer, the term of this patent is extended or adjusted under 35 U.S.C. 154(b) by 105 days.

This patent is subject to a terminal disclaimer.

(21) Appl. No.: 14/935,034

(22) Filed: Nov. 6, 2015

(65) Prior Publication Data

US 2016/0065912 A1     Mar. 3, 2016

Related U.S. Application Data

(63) Continuation-in-part of application No. 13/477,861, filed on May 22, 2012, now Pat. No. 9,200,890.

(51) Int. Cl.
*H04N 7/18* (2006.01)
*G06T 3/40* (2006.01)
(Continued)

(52) U.S. Cl.
CPC ............ *G06T 3/40* (2013.01); *G01B 11/04* (2013.01); *G01B 11/24* (2013.01); *G01N 21/8806* (2013.01); *G06T 7/001* (2013.01); *G06T 7/20* (2013.01); *G06T 7/70* (2017.01); *H04N 5/2353* (2013.01); *G03B 15/16* (2013.01);
(Continued)

(58) Field of Classification Search
CPC combination set(s) only.
See application file for complete search history.

(56) References Cited

U.S. PATENT DOCUMENTS 5,586,058 A   12/1996   Aloni et al.
5,940,296 A   8/1999    Meyer
(Continued)

FOREIGN PATENT DOCUMENTS

CN   101276218   10/2008
JP   04348050    12/1992
(Continued)

OTHER PUBLICATIONS

Harris, Ken. "An Application of IEEE 1588 to Industrial Automation." Article. Published by Rockwell Automation, Jan. 2009. pp. 1-6.
(Continued)

*Primary Examiner* — Janese Duley
(74) *Attorney, Agent, or Firm* — Quarles & Brady LLP

(57) ABSTRACT

Systems and methods trigger an image acquisition of an object using motion data communicated from a motion controller on a network, the motion controller coupled to a motion drive. Based upon motion data from the motion controller, a virtual axis application is used to plan the movement of a virtual axis for a motion cycle, the virtual axis allowing an acquisition trigger rate to be calculated to follow movement of the object caused by the motion drive. Based on the calculated acquisition trigger rate, an acquisition trigger signal is generated for triggering the image acquisition of the object.

20 Claims, 8 Drawing Sheets

(51) Int. Cl.

| | | |
|---|---|---|
| *G06T 7/00* | (2017.01) | |
| *G06T 7/20* | (2017.01) | |
| *G01B 11/04* | (2006.01) | |
| *G01B 11/24* | (2006.01) | |
| *G01N 21/88* | (2006.01) | |
| *H04N 5/235* | (2006.01) | |
| *G06T 7/70* | (2017.01) | |
| *G03B 15/16* | (2006.01) | |
| *H04N 5/232* | (2006.01) | |

(52) U.S. Cl.
CPC ............. *G06T 2207/30108* (2013.01); *H04N 5/23206* (2013.01)

(56) References Cited

U.S. PATENT DOCUMENTS

| | | | |
|---|---|---|---|
| 6,167,148 A | 12/2000 | Calitz et al. | |
| 6,504,611 B2 | 1/2003 | Kogan et al. | |
| 6,610,991 B1 | 8/2003 | Case et al. | |
| 7,529,599 B1 | 5/2009 | Bhatt et al. | |
| 7,656,751 B2 | 2/2010 | Rischar et al. | |
| 7,760,238 B2 | 7/2010 | Giesen | |
| 7,791,671 B2 * | 9/2010 | Schultz | H04N 5/23203 348/211.4 |
| 7,915,570 B2 | 3/2011 | Cetrulo et al. | |
| 8,145,338 B2 | 3/2012 | Kent et al. | |
| 8,687,060 B1 * | 4/2014 | Wolff | G06F 3/0304 250/206.2 |
| 2002/0177974 A1 | 11/2002 | Ting et al. | |
| 2008/0240321 A1 | 10/2008 | Narus et al. | |
| 2009/0144647 A1 | 6/2009 | Chandhoke | |
| 2010/0073665 A1 | 3/2010 | Zhao et al. | |
| 2011/0141269 A1 | 6/2011 | Varga et al. | |
| 2011/0199532 A1 | 8/2011 | Jin | |
| 2011/0297590 A1 * | 12/2011 | Ackley | B07C 5/3422 209/580 |
| 2012/0150336 A1 | 6/2012 | Kent et al. | |

FOREIGN PATENT DOCUMENTS

| | | |
|---|---|---|
| JP | 2011124759 | 6/2011 |
| WO | 2006021219 A1 | 3/2006 |

OTHER PUBLICATIONS

"ControlLogix Digital I/O Modules." User Manual. Published by Rockwell Automation, Aug. 2010. pp. 52-54.

"1732E ArmorBlock EtherNet/IP Dual Port 8-Point Sequence of Events Input and Scheduled Output Modules." User Manual. Published by Rockwell Automation, Feb. 2012. pp. 59-84.

* cited by examiner

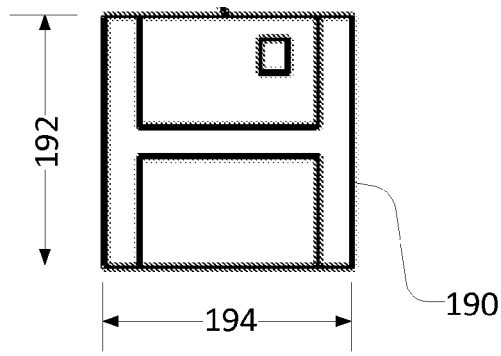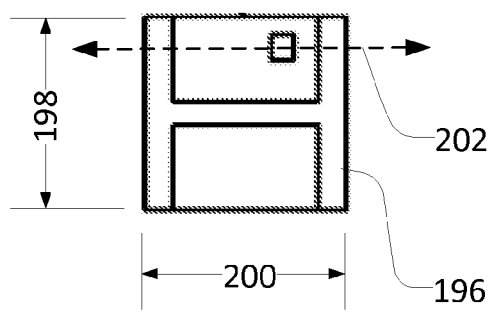
FIG. 5A                    FIG. 5B
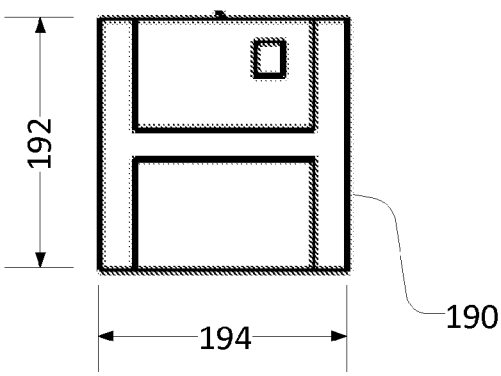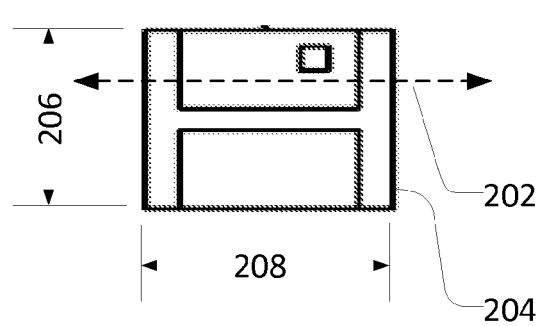
FIG. 6A                    FIG. 6B
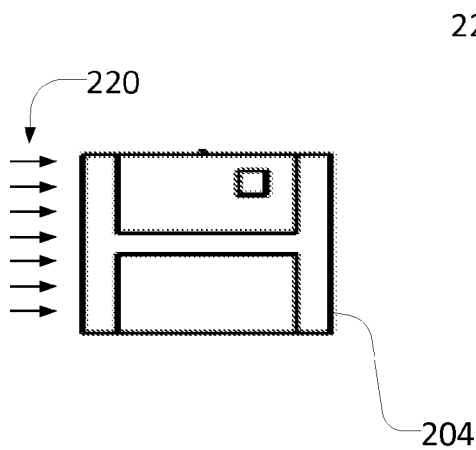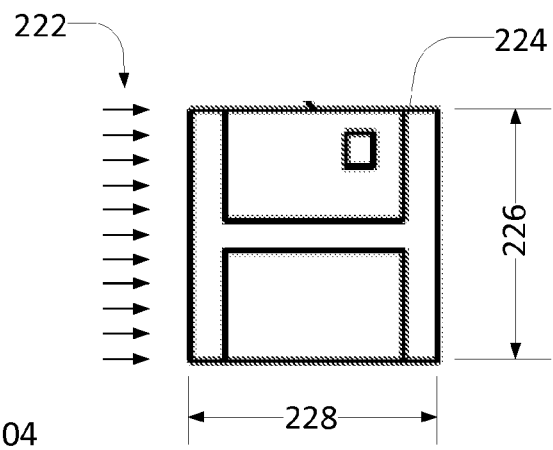
FIG. 7A                    FIG. 7B

MACHINE VISION SYSTEMS AND METHODS WITH PREDICTIVE MOTION CONTROL

CROSS-REFERENCE TO RELATED APPLICATIONS

This reference is a continuation-in-part of co-pending U.S. patent application Ser. No. 13/477,861, titled "Machine Vision Systems and Methods with Predictive Motion Control" and filed on May 22, 2012, which is incorporated herein by reference.

STATEMENT REGARDING FEDERALLY SPONSORED RESEARCH OR DEVELOPMENT

Not applicable.

BACKGROUND OF THE INVENTION

The present invention relates to vision systems, and more specifically, to a vision system coupled to a motion controller, the motion controller providing motion data used for generating an image acquisition trigger signal.

In many applications, machine vision or image processing analysis is used to inspect or locate an object. For example, in manufacturing applications, machine vision analysis may be used to detect defects in a manufactured object by acquiring images of the object and using various types of image processing algorithms to analyze the images. As an example, a system to manufacture an object such as a memory disk may use machine vision to examine the object in order to detect manufacturing defects, and ensure that the object is marked or assembled properly.

In such machine vision systems, an encoder is often used to communicate object position to the vision system in order to generate trigger signals at calculated times and to schedule the generation of digital outputs. The trigger signals are used to acquire one or more images of the object in the field of view as it moves in front of the vision system, and the digital outputs may be used for triggering a reject mechanism, for example. FIG. 1 shows an illustrative machine vision system 20 adapted to acquire one or more images 22 of a memory disk 24. Conveyor 28 transports the disks 24 to cause relative movement between the disks 24 and the field of view 30 of imaging device 32. Motion of the conveyor 28 is tracked by one or more encoders 36. The encoder 36 sends signals over link 40 to a controller 42 (e.g., a processor device), which uses the encoder signals to calculate disk position, and to generate a trigger signal over link 44 at calculated times to the imaging device 32 to acquire one or more images of the disk 24 in the field of view. If the disk 24 is defective, the imaging device 32 and/or the controller 42 may be programmed to send a signal over link 46 to a reject actuator 48 to remove the defective disk 50 from the conveyor 28 as shown.

In some cases, however, encoders can be troublesome and undesirable due to their inaccuracies, noise immunity issues, and reliability issues. Accordingly, in some cases, removing the need for a separate encoder to provide position data to the imaging device would improve overall performance for the machine vision system, reduce points of failure, and increase efficiencies for the vision system user.

BRIEF SUMMARY OF THE INVENTION

The present embodiments overcome disadvantages of the prior art by calculating object position using motion data from a motion controller.

Accordingly, some embodiments comprise a vision system for triggering an image acquisition of one or more objects using motion data communicated from a motion controller on a network, where the motion controller is coupled to a motion drive. The vision system comprises an image acquisition device. An acquisition controller is coupled to the image acquisition device, with the acquisition controller including a network interface, and the network interface operable to couple to the network. The acquisition controller, upon receiving motion data from the motion controller, uses a virtual axis application to plan the movement of a virtual axis for a motion cycle, the virtual axis allowing an acquisition trigger rate to be calculated by the acquisition controller that follows movement of the one or more objects caused by the motion drive. Based on the calculated acquisition trigger rate, the acquisition controller generates an acquisition trigger signal for triggering the image acquisition of the one or more objects.

Other embodiments comprise a vision system including an image acquisition device that is operable to trigger an image acquisition of one or more objects using motion data communicated from a motion controller on a network, with the motion controller being coupled to a motion drive. The image acquisition device is in communication with a virtual axis application and an acquisition controller, with the acquisition controller being coupleable to the network. A common time reference is provided by at least one of the motion controller, an image acquisition device clock, a dedicated master clock, and the motion drive. The image acquisition device, upon receiving the motion data communicated from the motion controller, uses the virtual axis application to plan the movement of a virtual axis for a motion cycle, the virtual axis operable to follow relative movement of the one or more objects caused by the motion drive. Based on movement of the virtual axis, the image acquisition device generates an acquisition trigger signal for triggering the image acquisition of the one or more objects.

Still other embodiments include a method for acquiring one or more images of one or more objects. The method comprises providing a common time reference to an image acquisition device and a motion controller, the image acquisition device and the motion controller being in communication on a network. The motion controller sends motion data to a motion drive, and sends the motion data over the network to the image acquisition device. Upon receiving the motion data, the image acquisition device plans the movement of a virtual axis, such that the virtual axis moves in a fixed relationship to the motion drive. Using the virtual axis, an image acquisition trigger rate is generated that virtually follows movement of the one or more objects. Using the image acquisition trigger rate, an image acquisition trigger signal is generated. The one or more images of the one or more objects are acquired using the image acquisition device.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE SEVERAL VIEWS OF THE DRAWINGS

FIG. 5A is a schematic view of a model of an object;

FIG. 5B is a schematic view of an image of the object corresponding to the model in FIG. 5A;

FIG. 6A is another schematic view of the model of FIG. 5A, similar to FIG. 5A;

FIG. 6B is a schematic view of another image of the object corresponding to the model in FIGS. 5A and 6A;

FIG. 7A is another schematic view of the image of FIG. 6B;

FIG. 7B is a schematic view of still another image of the object corresponding to the model in FIGS. 5A and 6A;

Figure 1:
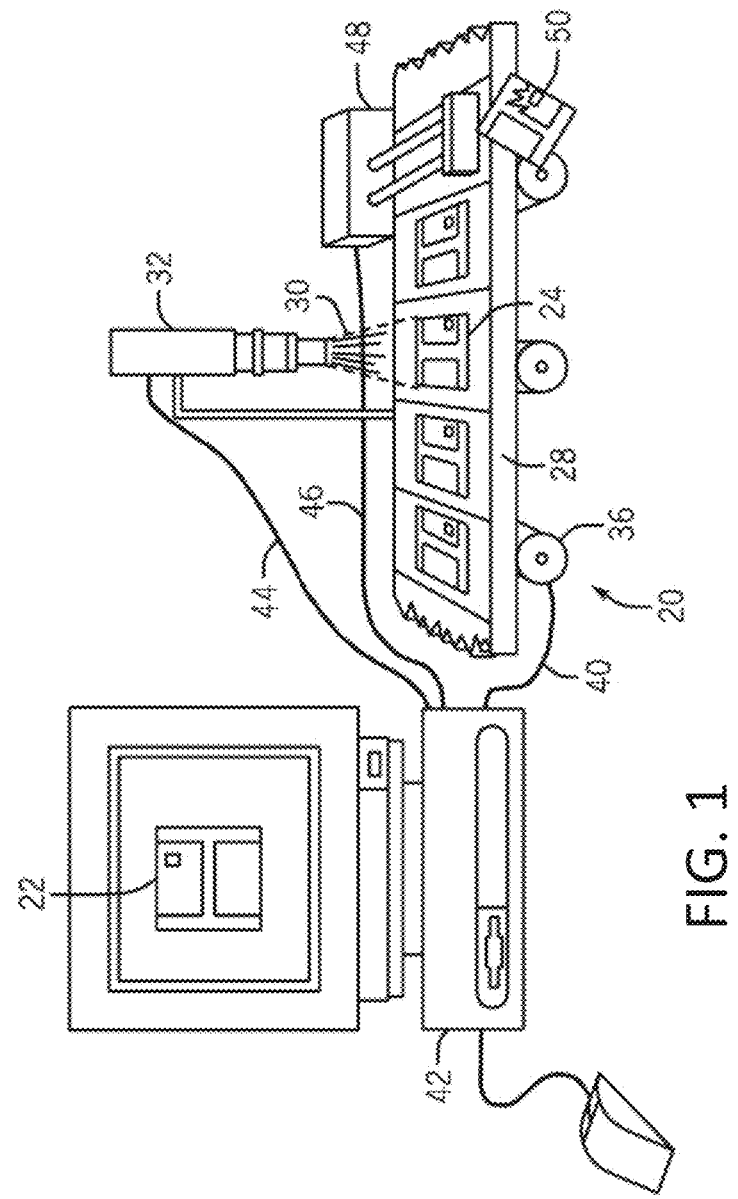
FIG. 1 is a schematic view of a typical vision system configuration including an encoder to provide encoder signals for calculating object position.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

The various aspects of the subject invention are now described with reference to the annexed drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system," "module," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components (or system, module, and so on) may reside within a process and/or thread of execution, may be localized on one computer, distributed between two or more computers or processors, and/or included within another component (or system, module, and so on).

The word "exemplary" is used herein to mean serving as an example, instance, or illustration. Any aspect or design described herein as "exemplary" is not necessarily to be construed as preferred or advantageous over other aspects or designs.

As used herein, phrases such as "at least one of A, B, and C," "one or more of A, B, and C," and the like, are meant to indicate A, or B, or C, or any combination of A, B, and/or C. This meaning will be understood also to apply to similar formulations with different numbers of elements (e.g., "at least one of A and B," "one or more of A, B, C, and D," and so on).

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to these configurations without departing from the scope or spirit of the claimed subject matter.

Embodiments of the invention are described below by using diagrams to illustrate either the structure or processing of embodiments used to implement the systems and methods of the present invention. Using the diagrams in this manner to present embodiments of the invention should not be construed as limiting of its scope. The present invention contemplates both systems and methods for calculating object position using data from a motion controller. The embodiments of the present invention may comprise a device, e.g., an automation device, a special purpose or general purpose computer including various computer hardware, software, and/or firmware, etc., as discussed in greater detail below.

Various embodiments of the invention will be described in connection with a machine vision system incorporating a smart camera configured to calculate an object's position using motion data from a motion controller. In some embodiments, the smart camera is configured to generate a virtual axis based on the motion data. That is because the features and advantages of the invention are well suited for this purpose. Still, it should be appreciated that the various aspects of the invention can be applied in other forms of imaging devices and in other systems that may have access to data from a motion controller.

An exemplary machine vision system may be used in a manufacturing assembly, test, measurement, automation, and/or control application, among others, as non-limiting examples. The exemplary machine vision system may use image acquisition software operable to perform any of various types of image acquisitions.

Figure 2:
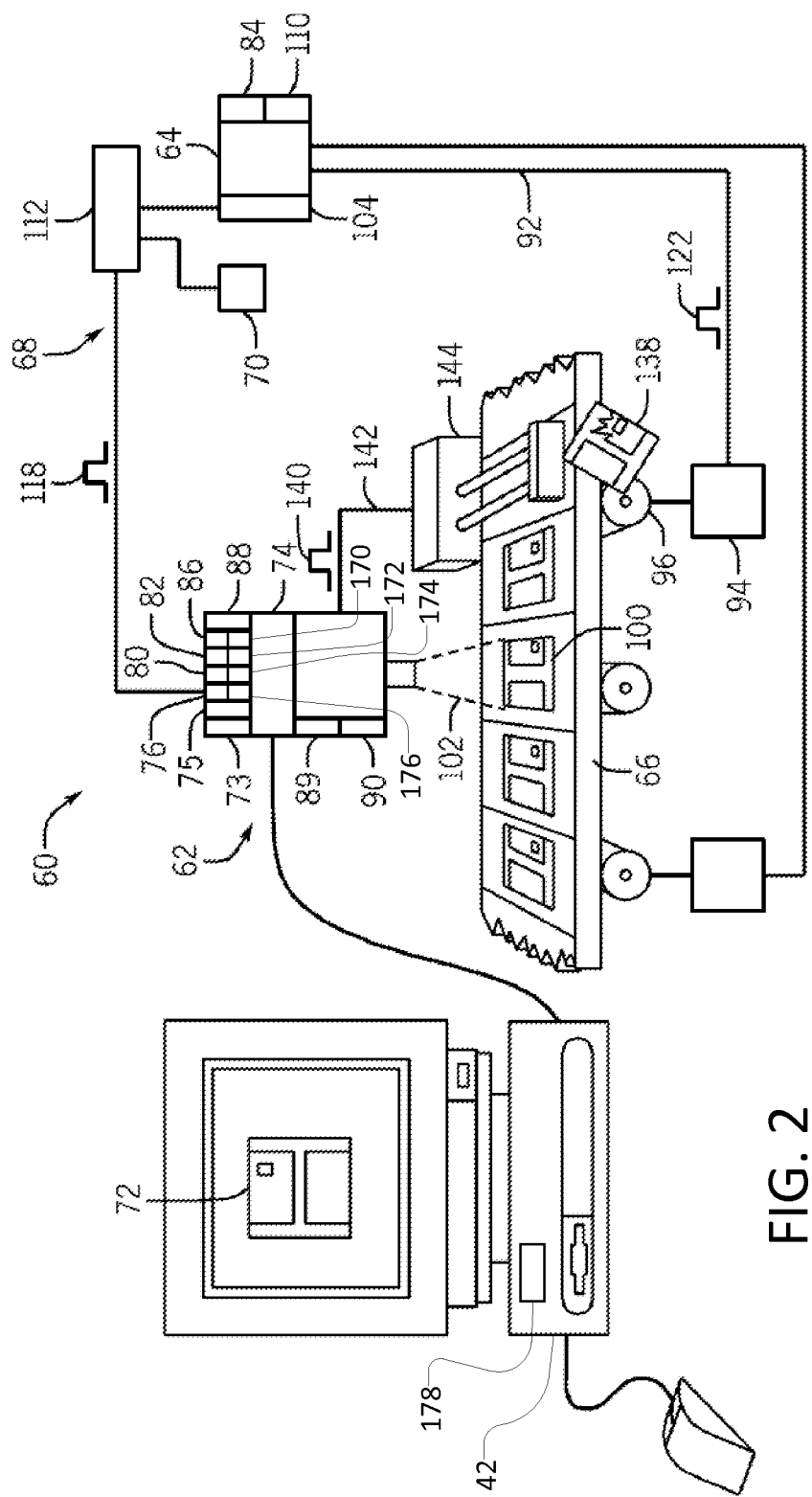
FIG. 2 is a schematic view of an exemplary vision system including a motion controller for providing motion data, the motion data used to generate a virtual axis, in accordance with the present embodiments.

Referring now to FIG. 2, an exemplary machine vision system 60 generally includes a smart camera 62, a motion controller 64 generally responsible for coordinating the movement of a movable system such as a robotic arm, a production line or conveyor 66, for example, and at least one communications network 68 to couple at least the smart camera 62 and the motion controller 64. In some embodiments, a dedicated master clock 70 may also be coupled to the network 68 to serve as a master time reference between devices on the network, including at least the smart camera 62 and the motion controller 64. In other embodiments, the motion controller 64 may serve as the master time reference. Each of these components will be described below in greater detail. It is to be appreciated that in other embodiments, one network, such as network 68 may be used for keeping devices on the network synchronized, while another network 78 may be used for the communication of motion data.

As used herein, the term "smart camera" is intended to include any of various types of image acquisition devices that are operable to acquire and/or store an image 72 and that include on-board processing capabilities. A smart camera may thus be operable to acquire and analyze or process the acquired or stored image. Examples of a smart camera include analog and digital cameras, line scan cameras, infrared imaging devices, x-ray imaging devices, ultra-sonic imaging devices, and any other type of device which operates to receive, generate, process, or acquire an image or sensor data. The smart camera may be stationary in use, or the smart camera may be mobile and may be moving while acquiring an image.

The smart camera 62 of machine vision system 60 may include an acquisition controller 74 for performing an image acquisition function as described below. The acquisition controller 74 may include a processor 73 and memory 75 or a programmable hardware element, for example. The acquisition controller 74 may also include a network interface 76 to couple the smart camera to the network 68. The acquisition controller 74 may include a smart camera adjustable clock 80, and a smart camera synchronization application 82 that is capable of keeping the smart camera adjustable clock 80 synchronized with a motion controller adjustable clock 84 (discussed below) on the network 68.

The acquisition controller 74 may also include a virtual axis application 86. In some embodiments, the virtual axis application generates a virtual axis 88 in memory 75 that can be controlled by the motion controller 64. In other embodiments, the motion controller 64 may provide motion data to the acquisition controller 74 that can be used to enable the virtual axis application 86. It is to be appreciated that components described as being a part of the acquisition controller 74 are also considered as part of the smart camera 62, and components described as being a part of the smart camera 62 are also considered as part of the acquisition controller 74.

The smart camera 62 may also include a processor 89 and a memory medium 90 on which computer programs may be stored and/or executed. In other embodiments, configuration information may be stored that may be used to configure a programmable hardware element, such as a field programmable gate array (FPGA), comprised in the smart camera to perform a calculation, measurement, control, automation, or analysis function, among others.

As used herein, the terms "memory" and "memory medium" includes a non-volatile medium, e.g., a magnetic media or hard disk, optical storage, or flash memory; a volatile medium, such as computer system memory, e.g., random access memory (RAM) such as DRAM, SRAM, EDO RAM, RAMBUS RAM, DR DRAM, etc.; or an installation medium, e.g., a CD-ROM, or floppy disks, on which the computer programs may be stored.

Motion of the conveyor 66 may be controlled by the motion controller 64, or more than one motion controller. The motion controller 64 sends position signals over a link 92 to control operation of a motion drive, such as servo drive 94 coupled to a servo motor 96, which in turn controls the motion of the conveyor 66. In some embodiments, the link 92 may be coupled to a network hub 112 (discussed further below) instead of directly to the motion controller. The motion controller 64 or the dedicated master clock 70, for example, may provide the common time reference for the servo drive 94.

In the exemplary vision system 60, more than one servo drive and motor may be used. Accordingly, the motion controller 64 may be responsible for coordinating the movement of the servo motor 96 on the conveyor so the conveyor 66 is able to transport one or more objects 100 to cause relative movement between the objects 100 and the field of view 102 of the smart camera 62.

Similar to the acquisition controller 74, or smart camera 62, the motion controller 64 may also include a network interface 104 to couple the motion controller to the network 68. The motion controller 64 may also include the motion controller adjustable clock 84, and a motion controller synchronization application 110 that is operable for keeping the motion controller adjustable clock 84 synchronized with the smart camera adjustable clock 80 across the network 68.

The smart camera 62 and the motion controller 64 are both coupled to the communications network 68. One example of a common communications network is a non-deterministic network, such as an Ethernet based network. Another example is a deterministic, low-latency network, such as an EtherCAT or PowerLink based network. Other possible communication networks would also be known to one skilled in the art. In this embodiment, a network hub 112 may be used to serve as a common connection point for the smart camera 62 and the motion controller 64 on the network 68.

As mentioned above, in some embodiments, a dedicated master clock 70 may also be coupled to the network 68. When used, the master clock 70 may serve as the dedicated clock between the devices on the network 68, either independent of or in conjunction with the smart camera adjustable clock 80 and the motion controller adjustable clock 84. The smart camera synchronization application 82 and the motion controller synchronization application 110 may also be capable of keeping the smart camera adjustable clock 80 and the motion controller adjustable clock 84 synchronized with the master clock 70 across the network 68.

Algorithms used to synchronize local clocks between devices on a non-deterministic network are described by the IEEE-1588 standard, which is incorporated herein by reference. Algorithms used to convert target position, velocity, and/or acceleration into a motion curve are documented under the ODVA CIP specification, which is also incorporated herein by reference. It is to be appreciated that one of skill in the art would understand the workings of both the IEEE-1588 standard and the ODVA CIP specification.

Figure 3:
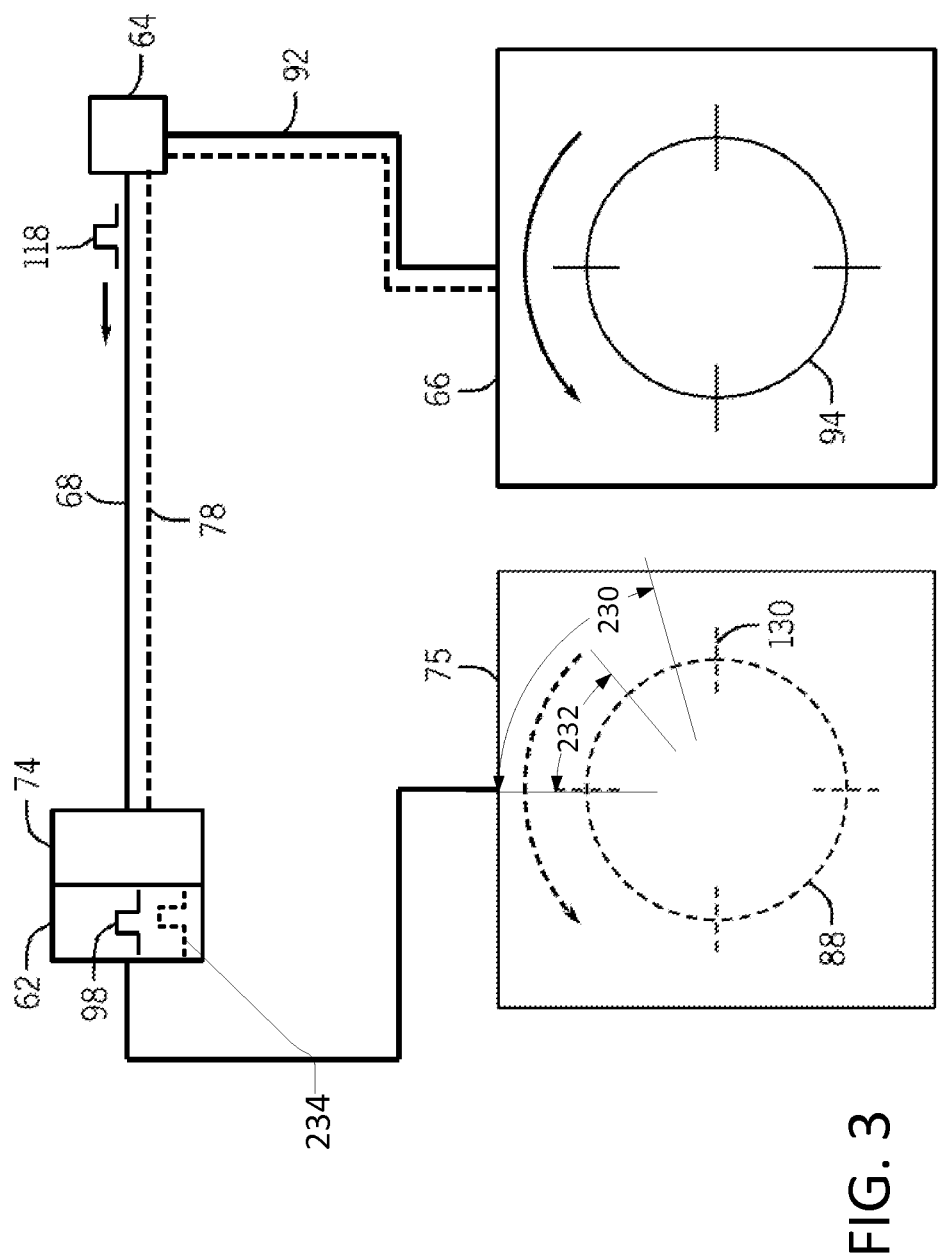
FIG. 3 is a schematic view, showing various vision system signals, and a virtual axis tracking a motion drive.

Referring to FIGS. 2 and 3, the motion controller 64 can send motion data 118 over the network 68 to the smart camera 62, in some embodiments via the acquisition controller 74, which uses the virtual axis application 86 in conjunction with the motion data to calculate object 100 position, and to generate a trigger signal 98 at calculated times for the smart camera 62 to acquire one or more images of the object 100 in the field of view 102.

As described above, the smart camera 62 and the motion controller 64 may utilize the smart camera synchronization application 82 and the motion controller synchronization application 110, respectively, along with the smart camera adjustable clock 80 and the motion controller adjustable clock 84, and/or the dedicated master clock 70, to generate a synchronized clock so as to create a common time reference between the smart camera 62 and the motion controller 64. This common time reference between the smart camera 62 and the motion controller 64 may be within about 10 usec., although more or less is contemplated.

At a frequency of between about 50 Hz to about 2500 Hz, or more or less, the motion controller 64 communicates motion data 122 to the servo drive 94. The motion data 122 may include a variety of parameters including a target position, target velocity, velocity limits, target acceleration, acceleration limits, and/or a time at which the target should reach a target position and/or velocity. Motion data may also include other data parameters, some of which are described by the IEC 61800-7 standard, which is incorporated herein by reference. The motion controller 64 may also transmit motion data to the smart camera 62 over the network 68, or a separate network. The time may be implied rather than transmitted, such as where nodes, e.g., devices, on the network are synchronized by fixed cycles on the network, and implicitly any command takes effect on the start of a subsequent motion cycle.

For every motion cycle, in some embodiments, the motion controller 64 determines the motion data for the next motion cycle, and communicates the motion data for the next motion cycle to the smart camera 62 in a message 124. The smart camera 62, upon receiving the message 124, may use the virtual axis application 86 to plan the movement of a virtual axis 88 for the next motion cycle. One of skill in the art would recognize that different motion networks and different motion controllers may have differing rules for how the motion data is defined, how the motion data is transmitted on the network, and how movement of an axis is determined from the motion data.

Based on the motion data, the virtual axis 88 is generated by the virtual axis application 86. The virtual axis 88 serves to move in a fixed relationship to the servo drive 94. In some embodiments, the motion controller "gears" the virtual axis 88 based on the servo drive axis such that when the virtual axis reaches a certain position, the object 100 is in the field of view 102 of the smart camera 62, and an image acquisition can be triggered. In other embodiments, the motion controller 64 may indicate to the smart camera 62 the position of the virtual axis 88 when the object 100 will be in the field of view 102. This may be based on other sensors connected to the motion controller 64 detecting the position of the object on the conveyor 66. From the virtual axis 88, a user-specified multiplier 130 may be used to generate an image acquisition trigger rate 132 that virtually follows the movement of the object 100 on the conveyor 66. For example, one revolution of the virtual axis may define one part cycle as is seen by the camera 62, and the camera may want to acquire three images of the part, a user could specify that the acquisition trigger is to be signaled every 120 degrees. Similarly, for a line scan camera, a user may want to acquire a single line every 0.5 degrees in order to acquire exactly 720 lines of the part.

Based on the calculated image acquisition trigger rate 132, the smart camera 62 generates the image acquisition trigger signal 98 at a frequency relative to the object movement commanded by the motion controller 64 to the servo drive 94. Because the smart camera 62, motion controller 64, and servo drive 94 are all synchronized by a common time base, the smart camera 62 may be able to generate the image acquisition trigger signal 98 that is close, within acceptable limits, to the actual object movement without the use of a hardware encoder.

In some embodiments, the machine vision system 60 may be configured to detect a defective object 138. When an object is defective, the smart camera 62 and/or the motion controller 64 may be programmed to send a fail signal 140 over link 142 to a reject actuator 144 to remove the object 138 from the conveyor 66. The fail signal 140 can be generated by the time the object to be rejected arrives at the reject actuator 144 farther down the conveyor from the smart camera 62. In order to generate the fail signal 140 in the presence of conveyor speed changes, the smart camera 62 can determine how fast the conveyor 66 is moving. The smart camera 62 synchronized to the motion controller 64 as described above would be able to precisely generate the fail signal 140 when the object arrived at the reject actuator 144 regardless of line speed. This configuration may be applied to any output from the smart camera 62 that may be synchronized with conveyor movement.

The components of the exemplary machine vision system 60 described above are configured such that the smart camera 62 is able to coordinate the generation of an image acquisition trigger with the motion of the object 100 being inspected on the conveyor 66, based on motion data from the motion controller, and without the smart camera 62 sending any motion data to the motion controller.

Figure 4:
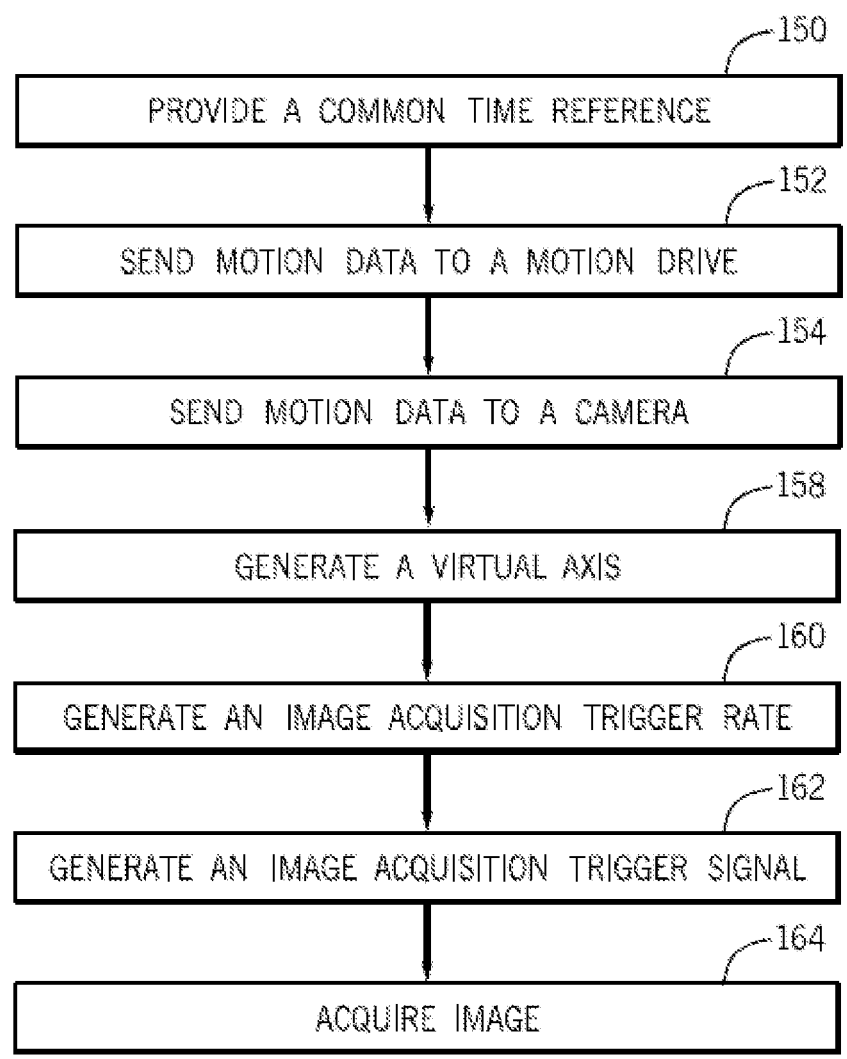
FIG. 4 is a flow chart of a method in accordance with the present embodiments.

FIG. 4 illustrates an embodiment of a method for triggering line acquisitions of a smart camera using servo motor motion data communicated from a networked motion controller for acquiring an image of the object. The method shown in FIG. 4 may be used in conjunction with any of the systems or devices shown in the above Figures, among others. In various embodiments, some of the method elements shown may be performed concurrently, in a different order than shown, or may be omitted. Additional method elements may also be performed as desired.

Referring to FIG. 4, a method is shown for acquiring an image of an object. A first step is to provide a common time reference to the smart camera 62 and the motion controller 64, as indicated at process block 150. As previously described, the smart camera and the motion controller can be in communication via the network 68. At process block 152, the motion controller sends a motion data signal to a motion drive. The motion data signal may be sent over link 92, or across the network 68, for example. At process block 154, the motion controller sends the motion data over the network 68 to the smart camera 62. Upon receiving the motion data, the smart camera 62 uses the virtual axis application 86 on the smart camera 62 to generate a virtual axis 88 in memory 75 from the motion data, with the virtual axis 88 moving in a generally fixed relationship to the servo drive 94, as indicated at process block 158. Using the virtual axis 88, an image acquisition trigger rate can be generated that virtually follows relative movement of the object 100, as indicated at process block 160. Using the image acquisition trigger rate, an image acquisition trigger signal can be generated, at process block 162, and the smart camera may acquire an image of the object 100, as indicated at process block 164. The image acquisition trigger signal may be generated at a frequency relative to the object movement commanded by the motion controller.

In some situations, images acquired for use by a machine vision system can exhibit characteristics that may not be favorable to analysis of the images by machine vision tools or interaction with the images by users of the machine vision system (e.g., visual assessment of the images by different users). For example, if a sampling rate of a line scan camera (or similar other image acquisition device) is not appropriately synchronized with movement of an object past the camera, an image compiled from successive line scans by the camera may not fully represent the object. Further, due to the omission of parts of the object from the compiled image, dimensions of the image (e.g., linear dimensions, aspect ratios, and so on) may be distorted from the actual dimensions of the object. For example, where a sampling rate of a line scan camera is slower than appropriate, an image of an object may be shortened along the direction of object motion, relative to the actual dimensions of the object. As another example, similar (and other) issues can arise if an image acquisition device becomes misaligned with a desired field of view (e.g., is moved closer to or farther from a target imaging area).

The sampling rate of an image acquisition device can fall out of synchronization with object movement for a variety of reasons. In some cases, a lack of synchronization can result from transient or other phenomenon in devices for moving the relevant object (e.g., the conveyor 66, the servo motor 96, and so on). These phenomenon can include, for example, transient motion phenomenon such as jitter (i.e., generally unexpected or undesirable movement, such as intermittent jerks, pauses, vibration and so on) and slack (e.g., constant, cyclical, or other stretching during operation).

In some implementations, a machine vision system according to this disclosure can be configured to identify issues in image capture and analysis that may result from transient and other phenomenon relating to object movement (e.g., jitter and slack). Once a particular issue (or an effect thereof) has been identified, the system can then implement appropriate corrective measures. For example, as also discussed below, the machine vision system 20 can compare an acquired image of an object with a reference model in order to identify deviations of the acquired image from the model. Based on this comparison, the machine vision system 20 can then identify issues such as mis-calibrated sampling rates for image capture, transient or other movements of the conveyor 66 or other motion systems, and so on. The machine vision system 20 can then implement corrective measures, such as adjustment of sampling rates for image capture, various post-processing or other operations on acquired images or aspects of the machine vision system 20 itself (e.g., one or more machine vision tools), or transmission of error messages to system users.

In the discussion herein, some examples are presented in the context of the machine vision system 20 as a whole. Some examples are presented in the context of particular hardware, applications, or other modules of the machine vision system 20. It will be understood that these examples are not intended to be limiting with respect to the particular system, sub-system, application, or other module that can be used to execute particular functionality. For example, some discussion below presents image analysis and other functionality as implemented by modules of the camera 62. It will be understood that this (and other) functionality can additionally (or alternatively) be implemented with other image acquisition devices, or other modules (e.g., hardware, software, and so on that are not included in the camera 62) of the machine vision system 20.

Consistent with the discussion above, the camera 62 can include a number of modules, which can be implemented as software, as hardware, as a combination of software and hardware, or in other ways. In some embodiments, referring to FIG. 2, these modules can include a comparison module 170, a reporting module 172, a post-processing module 174, and a tool adjustment module 176. These modules 170, 172, 174 and 176 can be in communication with various other modules (e.g., other hardware or software applications) of the machine vision system 20. For example, the tool adjustment module 176 can be in communication with a tool module 178 linked to the processor 42, which can include one or more machine vision tools (e.g., edge-finding tools, shape-recognition tools, scaling and shape-manipulation tools, 1-D and 2-D code reading tools, character recognition and validation tools, pattern-matching tools, including model-based shape recognition tools, and so on). As also discussed generally above, in some embodiments, the modules 170, 172, 174, and 176 can be combined with each other or with other modules, or can be included on other system components (e.g., as part of the motion controller 64, acquisition controller 74, and so on).

In some implementations, in order to analyze an acquired image (or images) of an object, the machine vision system 20 can access (e.g., from memory medium 90) a virtual model (or, herein, simply "model") of the object. Generally, a model can usefully represent relevant aspects of an ideally acquired image of a particular part. For example, a model for an object can generally include expected locations of geometrical features and other geometrical aspects (e.g., locations of corners, edges, pattern-matches, text/code, holes, or other features, and so on) of an idealized image of the memory disk 24 (e.g., an image acquired under appropriately controlled circumstances). In some cases, one or more of these geometrical features and other geometrical aspects, alone or in various combinations, can exhibit expected aspect ratios. Accordingly, as illustrated in FIG. 5A, a model 190 of the object 100 can represent various geometrical aspects of the object 100, including a length 192 and a width 194, and the corresponding aspect ratio (e.g., a ratio of the length 192 to the width 194).

It will be understood, unless otherwise noted, that "length," "width," and similar terms used herein are chosen for convenience only, and are not intended to denote an absolute orientation of an object or model. Similarly, examples below address the "bulk" aspect ratio of the object 100 (i.e., the ratio of the entire length 192 of the object 100 to the entire width 194 of the object 100). It will be understood that this aspect ratio is presented only as an example. In some implementations, an aspect ratio can be calculated in other ways (e.g., as the ratio of the width 194 to the length 192). In some implementations, aspect ratios can be calculated from other dimensions of the object 100, including from lengths and widths (or other dimensions) of particular parts and sub-parts of the object 100. In some implementations, a rotational operation (e.g., bulk rotation of an image of the object 100) can be executed as part of the calculation of a relevant aspect ratio (e.g., if the image of the object 100 is rotated relative to an expected orientation).

In some implementations, a model of an object can be created based upon an acquired image (or images) of a reference object, such as a calibration target or manufacturing blank. For example, the model 190 can be created based upon a series of line scans of a calibration target (not shown) by the smart camera 62. In such a case, it may be useful to acquire such an image under carefully controlled circumstances (e.g., with enhanced control or monitoring of the movement of the conveyor 66), such that the reference image that informs the model 190 represents the relevant object with appropriate accuracy. In some implementations, a model of an object can be constructed in other ways. For example, a user can manually (or otherwise) provide various relevant aspects of an object (e.g., bulk length and width, location and size of relevant features, and so on), from which a corresponding model of the object (e.g., a virtual object) can be constructed.

Once the model 190 (or another relevant model) has been created, an acquired image of a particular object (e.g., the object 100 (see FIG. 2) can be compared with the model 190 in order to identify any deviation of the acquired image from the model 190. Generally, a deviation from a model can include any variety of differences, including differences in overall dimensions, differences in aspect ratios (in bulk, or of specific parts), locations of edges and corners, and so on. As also discussed below, the identification of any deviations of an acquired image from a relevant model can usefully indicate issues with the image acquisition process or equipment.

In some implementations, comparison of an acquired image with a model can be executed by the comparison module 170. Comparison of images and models can be executed in various ways, and can sometimes include comparison of geometrical aspects of the image and the model. For example, in some implementations, the comparison module 170 can compare image data (e.g., pixel values) for an image 196 of the object 100 (see FIG. 5B) with corresponding data from the model 190, in order to assess whether a particular linear dimension or aspect ratio of the image 196 matches a corresponding linear dimension or aspect ratio of the model 190. For example, the comparison module 170 can identify a length 198 and a width 200 of the image 196 and compare these quantities, as well as the aspect ratio defined by the length 198 and the width 200, with the length 192, width 194, and corresponding aspect ratio of the model 190.

In the implementation illustrated in FIGS. 5A and 5B, comparison of geometrical aspects of the image 196 and the model 190 can reveal that the length 198 and the width 200 to be generally smaller than (i.e., deviate from) the corresponding length 192 and width 193 of the model 190. Similarly, the bulk aspect ratio of the image 196 (i.e., the length 198 divided by the width 200) is generally smaller than (i.e., deviates from) the corresponding aspect ratio of the model 190 (i.e., the length 192 divided by the width 190). The comparison module 170 can identify these deviations (and others) using various known techniques, including pixel analysis, edge- and corner-finding algorithms, shape detection, pattern location, optical character recognition, 1-D and 2-D symbol decoders, and so on. In other implementations, other deviations can be identified.

In some implementations, identified deviations between the image 196 and the model 190 can indicate various potential problems with the image acquisition that resulted in the image 196. As illustrated in FIG. 5B, for example, the width 200 of the image 196 is taken in parallel with a line-scan axis 202 for the smart camera 62. Where (as illustrated) the width 200 of the image 196 is smaller than the width 194 of the model 190, this can indicate that the smart camera 62 may have been improperly moved away from the conveyor 66. Similarly, the width 200 being larger than the width 194 (not shown) can indicate that the smart camera 62 may have been moved closer to the conveyor 66). Other deviations (e.g., distortions) can similarly indicate mis-alignment (e.g., angular misalignment) or other unexpected movement of the smart camera 62, or other components of the machine vision system 20.

In some implementations, the length 198 of the image 196 being smaller than the length 192 of the model 190 can indicate that the object 100 did not move past the smart camera 62 as anticipated (e.g., moved through the field of view 30 more quickly than anticipated), or that the sampling rate for the smart camera 62 (e.g., the rate controlling successive line scans by the smart camera 62) may not be properly calibrated with the actual motion of the object 100 (e.g., as controlled by the motion controller 64). Similarly, if the length 198 were larger than the length 192 (not shown), this may indicate that the object 100 did not move past the smart camera 62 as anticipated (e.g., moved through the through the field of view 30 more slowly than anticipated), or that the sampling rate for the smart camera 62 may not be properly calibrated with the actual motion of the object 100.

In some implementations, a combination of identified deviations of the image 196 from the model 190 can provide useful information regarding the acquisition of the image 196. For example, as also noted above, the comparison module 170 can compare the aspect ratio of the image 196 (e.g., the length 198 divided by the width 200) with the aspect ratio of the model 190 (e.g., the length 192 divided by the width 200). If the aspect ratios are the same, despite the differences between the respective pairs of lengths 192 and 198 and widths 194 and 200, this may indicate that some deviation between the image 196 and the model 190 results from a mis-alignment or improper movement of the smart camera 62, rather than necessarily from a non-ideal movement of the object 100 during acquisition of the image 196 or an improperly calibrated sampling rate for the smart camera 62. For example, if the smart camera 62 has been improperly or unexpectedly moved away from the conveyor 66, the aspect ratio of the image 196 may still match the aspect ratio of the model 190, even if particular dimensions of the image 196 (e.g., the length 198 and the width 200) do not match particular dimensions of the model 190 (e.g., the length 192 and the width 194).

In some cases, other deviations from a model can be possible. Referring to FIGS. 6A and 6B, for example, the comparison module 170 can compare another image 204 of the object 100 with the model 190. As illustrated, such a comparison can indicate that a length 206 of the image 204 is somewhat smaller than the model length 192, whereas a width 208 of the image 204 along the line scan axis 202, is substantially the same as the width 194. Accordingly, an aspect ratio of the image 204 (e.g., the length 206 divided by the width 208) will be somewhat smaller than the corresponding aspect ratio of the model 190. In some circumstances, this deviation in aspect ratios can indicate that the object 100 did not move past the smart camera 62 as anticipated, or that the sampling rate for the smart camera 62 may not be properly calibrated with the actual motion of the object 100. Further, the lack of deviation of the width 194 from the 208 may indicate that the smart camera 62 is still located in the expected position, relative to the conveyor 66.

Consistent with the discussion above, the deviation of the length 206 from the length 192 (and the corresponding deviation in aspect ratios) can potentially indicate undesirable phenomenon in the movement of the object 100 past the smart camera 62. For example, in some embodiments, the conveyor 66 can be subjected to jitter (e.g., generally unexpected or undesirable movement, such as intermittent jerks, pauses, vibration and so on). Such jitter can cause the object 100 to move unexpectedly, such that the sampling rate used by the smart camera 62 to capture the image 204 is not appropriately matched to the actual movement of the object 100. For example, jitter transmitted via the conveyor 66 can cause the object 100 to jerk forward unexpectedly (or lag unexpectedly) during image acquisition. Where the sampling rate used to acquire the image 204 is configured to match relatively constant movement of the object 100 (e.g., using the virtual axis 88, as described above), this jerking (or lagging) can result in portions of the object 100 not being imaged (or being imaged duplicatively) by the smart camera 62. Accordingly, when line scans from the image acquisition are combined into the image 204, the total image length 206 may be somewhat shorter (or longer) than the model length 192.

As another example, in some embodiments, the conveyor 66 (or related systems) can exhibit varying degrees of slack (e.g., constant, cyclical, or other stretching during operation). Such slack, for example, can cause the object 100 to lag behind its expected position, such that an image of the object 100 may be longer than expected (e.g., if the object lags during imaging).

In some cases, the movement of the object 100 may be subject to a combination of jitter and lag, which may result in various detrimental effects on the imaging of the object 100 (e.g., shortening or lengthening of aspects of the images 196 and 204). In some cases, phenomenon other than jitter or lag can also affect image acquisition, alone or in combination with jitter or lag.

When a deviation of an acquired image from a model is identified (e.g., the deviation of the image 196 or 204 from the model 190), it may be useful to alert a user to the possibility of a corresponding problem in the machine vision system 20. In some implementations, the reporting module 172 can accordingly generate and transmit an appropriate report (e.g., for display on a fixed-location monitor or mobile computing device (not shown)). As one example, referring again to FIG. 5B, where deviation of the image 196 from the model 190 suggests that the smart camera 62 may have been unintentionally moved with respect to the conveyor 66, it may be useful to transmit a report alerting a user to this possibility. In some cases, such a report can include a simple notification of the problem (e.g., a message alerting the user to a particular deviation between the image 196 and the model 190). In some cases, such a report can include suggested remedial measures. For example, the deviation of the aspect ratio of the image 196 from the model 190 (see FIGS. 5A and 5B) can be correlated to an estimated amount of movement of the smart camera 62. The corresponding report transmitted by the reporting module 172 can accordingly include a suggested re-location of the smart camera by the estimated amount. As another example, if a deviation of an image from a model suggests slack, jitter, or other issues with the conveyor 66 (and other associated systems), the reporting module 172 can include a message alerting a user to this possibility, as well as possible remedial measures.

In some implementations, processes for image acquisition can be adjusted based upon the comparison of an image to a model and the resulting identification of deviations between the image and the model. For example, where deviations of an image from a model suggest that a sampling rate for line-scan image acquisition is not appropriately correlated with actual object movement, an updated sampling rate can be calculated and implemented (or suggested to a user by the reporting module 172), such that a subsequent image acquisition results in an image that may deviate less from the relevant model.

In some implementations, as illustrated in FIG. 7A, the image 204 may have been captured from the object 100 with a series of line scans 220 at a particular sampling rate. Due to mis-calibration of the conveyor 66 or the machine vision system 20 generally, or due to other factors (e.g., slack, jitter, and so on), the sampling rate for the line scans 220 may have been too slow to appropriately capture the object 100. As a result, the image 204 exhibits a bulk aspect ratio that deviates from the corresponding bulk aspect ratio of the model 190. Based upon this deviation, the degree to which the old sampling rate for image acquisition was too slow can be identified (e.g., by dividing one of the relevant model aspect ratios by the corresponding image aspect ratio). A new sampling rate can then be calculated (e.g., by the comparison module 170), that will result in an appropriately larger number of line scans for a subsequent image acquisition (e.g., a subsequent image acquisition of another object similar to the object 100). As illustrated in FIG. 7B, for example, the line scans 222 can be executed with a sampling rate that was determined based upon the comparison of the image 204 and the model 190. As a result, an image 224 can be acquired, with the image 224 exhibiting a length 226, a width 228, and a corresponding aspect ratio that do not significantly deviate from the length 192, the width 194 and the corresponding aspect ratio of the model 190.

An updated sampling rate (e.g., as described above) can be implemented in various ways. In some cases, an updated sampling rate can be implemented using a virtual axis application, such as the virtual axis application 86 (and associated other modules) discussed above. Referring again to FIG. 3, for example, based upon an identified deviation of an image from a model, the smart camera 62 can use the virtual axis application 86 to generate an image acquisition trigger rate that virtually follows the actual movement of the object 100 on the conveyor 66. Notably, because it can be calculated based upon identified deviations between a previously acquired image and a relevant model (e.g., as discussed above), such an updated acquisition trigger rate can account for phenomenon that resulted in the identified deviation between the image 204 and the model 190 (e.g., jitter, slack, initial mis-calibration of the sampling rate, improper movement of the smart camera 62, and so on).

For example, the image 204 (see FIG. 6B) may have been captured using an acquisition trigger rate that corresponded to a line scan capture for every angular interval 230 in the virtual rotation of the virtual axis 88. Based upon the identified deviation between the aspect ratios of the image 204 and the model 190 (as also described above), this acquisition trigger rate can be determined to have been too slow for a complete imaging of the object 100. Accordingly, based upon the identified deviation between the image 204 and the model 190, a new acquisition trigger rate can be determined that corresponds to a line scan capture for every angular interval 232 in the virtual rotation of the virtual axis 88. With the virtual axis 88 virtually rotating at a similar rate as before (e.g., a rate that is geared to the rotation of the servo drive 94), the smaller angular interval 232 can result in the capture of an increased number of line scans during transit of the object 100 (or another object) past the smart camera 62.

With an updated acquisition trigger rate having been determined (e.g., as described above), the smart camera 62 can then generate an updated image acquisition trigger signal 234, which can prompt the smart camera 62 to acquire one or more images of the object 100 (or another object) in the field of view 102. Referring again to FIGS. 7A and 7B, for example, such an updated image acquisition trigger signal 234 can result in the capture of the image 224 using the line scans 222, with a sampling rate that is more closely aligned with the actual movement of the object 100 (or another object) and that accordingly produces the image 224 with a more appropriately scaled aspect ratio (or other aspect) relative to the model 190.

In some implementations, the comparison of images to models and subsequent determination of updated sampling rates (as appropriate) can be repeated with any particular frequency (or even irregularly) during a machine vision operation. For example, in some implementations, such comparison can be implemented for each image in a series of captured images, with updated sampling rates being determined (as appropriate) for each respective subsequent image acquisition. In some implementations, such comparison and updating of sampling rates can be implemented as part of an initial (or other) system calibration, or as requested by a user. This can be useful, for example, in order to calibrate the machine vision system 20 to generally produce images for analysis that exhibit a square-pixel scaling.

Figure 8A:
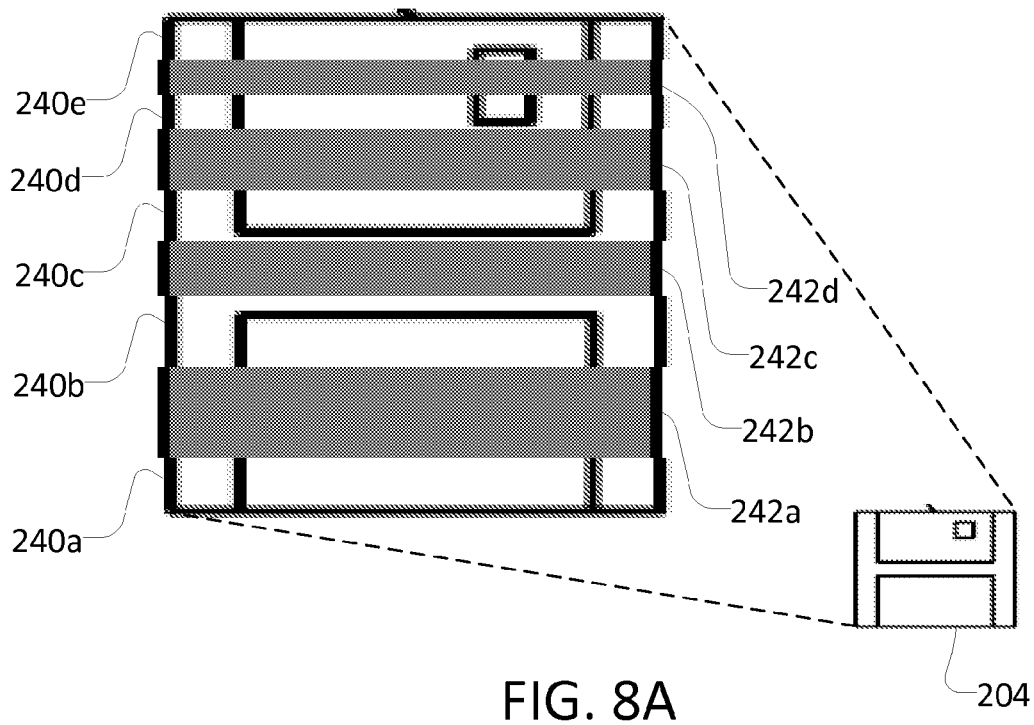
FIG. 8A is a schematic view of aspects of a modification of the image of FIGS. 6B and 7A.

In some implementations, comparison of an acquired image to a model can be used to inform post-processing of the acquired image itself, rather than (or in addition to) informing updates to sampling rates for subsequent image acquisitions. As illustrated in FIG. 8A, for example, the machine visions system 20 (e.g., via the comparison module 170) can identify that the image 204 is formed from a series of imaged lines 240a through 240e (e.g., with the lines 240a through 240e representing respective line scans of one-pixel width, relative to the direction of motion of the object 100 (see FIG. 2)). Based upon comparison of the image 204 with the model 190, and the resulting identification of a deviation of the length 206 from the length 192, the comparison module 170 (or other module of the machine visions system 20) can determine that the image 204 does not capture some aspects of the object 100. The post-processing module 174 (see FIG. 2) can then modify image data (e.g., pixel data) for the image 204 in order to correct for this deficiency and thereby prepare the image 204 for processing by various machine vision tools (e.g., as included in the tool module 178). As noted above, such modification can be implemented as an alternative, or in addition, to calculation of an updated sampling rate for subsequent image acquisition.

In some implementations, the post-processing module 174 can modify the image 204 by post-processing (e.g., resampling) image data for the image 204 to account for missing pixel data. As illustrated, for example, the post-processing module 174 can determine, based upon the comparison of the image 204 with the model 190, that portions of the object 100 represented by the imaged lines 240a through 240e are separated from each other by non-imaged portions of the object 100 (e.g., as represented by the blank lines 242a through 242d in FIG. 8A). The post-processing module 174 can then adjust the image 204 such that the appropriate, re-scaled aspect ratio (or other aspect) is obtained. For example, using one or more of various techniques, such as smoothing, adding, stretching, combining, duplicating, or otherwise processing pixels and pixel sets, the post-processing module 174 can fill in the blank lines 242a through 242d, such that an updated image 244 exhibits a length 246 and a width 248 (and a corresponding aspect ratio) that appropriately correlate to the model 190.

In some implementations, such post-processing of an image (and other operations) can be executed based upon a corrected sampling rate for subsequent image acquisitions (e.g., determined as described above). For example, where comparison of the image 204 and the model 190 indicates that an ideal sampling rate for image acquisition should be twice the actual sampling rate, the post-processing module 174 can adjust the image 204 to include approximately one additional line (e.g., one additional line of one-pixel width) for each actual line (e.g., each line 240a) from the image acquisition.

Figure 9A:
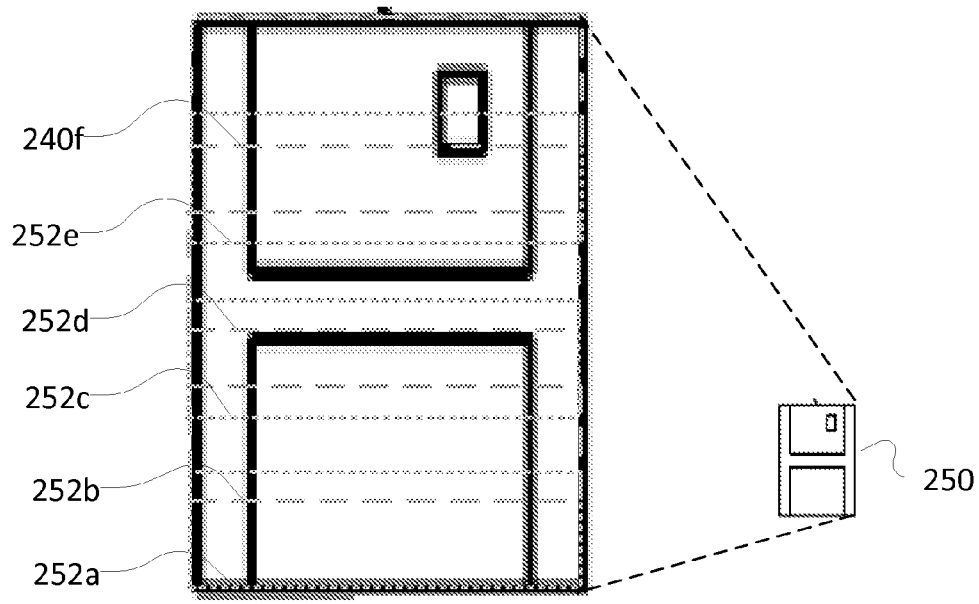
FIG. 9A is a schematic view of aspects of a modification of yet another image of the object corresponding to the model in FIGS. 5A and 6A.

In some implementations, the post-processing module 174 can modify an image to remove duplicate (or other excess) pixel data. As illustrated in FIG. 9A, for example, an image 250 may have been captured from the object 100 with a series of line scans at a particular sampling rate. Due to mis-calibration of the conveyor 66 or the machine vision system 20 generally, or due to other factors (e.g., slack, jitter, and so on), the sampling rate for the relevant line scans may have been too fast, and the image 250 may accordingly include line scans that overlap each other relative to the direction of movement of the object 100 (e.g., resulting in imaged lines 252a through 252f, depicted in FIG. 9A as rectangles with alternating types of dashed lines), or that otherwise include duplicative data. As a result, the image 250 exhibits a bulk aspect ratio that deviates from the corresponding bulk aspect ratio of the model 190 (see, e.g., FIG. 5A). Based upon this deviation, the degree to which the old sampling rate for image acquisition was too fast can be identified (e.g., by dividing one of the relevant model aspect ratios by the corresponding image aspect ratio), and, if appropriate, a new sampling rate can be calculated (e.g., by the comparison module 170), that will result in an appropriately smaller number of line scans for a subsequent image acquisition (e.g., a subsequent image acquisition of another object similar to the object 100).

Figure 9B:
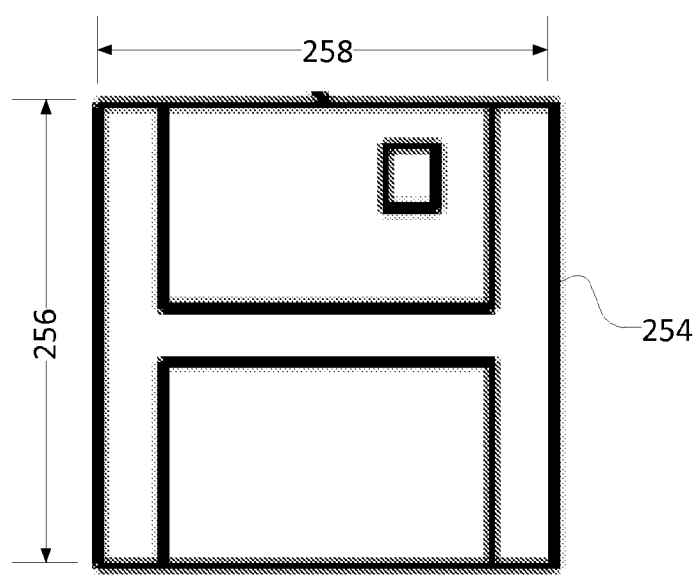
FIG. 9B is a schematic view of a modified image after the modification partially illustrated in FIG. 9A.

Further, for example, the post-processing module 174 can determine, based upon the comparison of the image 250 with the model 190, that portions of the object 100 represented by some of the imaged lines 252a through 252f are duplicates of portions of the object 100 that are represented by others of the imaged lines 252a through 252f. The post-processing module 174 can then adjust the image 250 appropriately, such that duplicate image data can be reduced or removed and the appropriate, re-scaled aspect ratio (or other aspect) is obtained. For example, using one or more of various techniques, the post-processing module 174 can delete duplicate pixel data (or merge duplicative portion of the imaged lines 252a through 252f together), such that an updated image 254 (see FIG. 9B) exhibits a length 256 and a width 258 (and a corresponding aspect ratio) that appropriately correlate to the model 190.

In some implementations, such post-processing of an image (and other operations) can be executed based upon a corrected sampling rate for subsequent image acquisitions (e.g., determined as described above). For example, where comparison of the image 250 and the model 190 indicates that an ideal sampling rate for image acquisition should be half the actual sampling rate, the post-processing module 174 can adjust the image 250 to include approximately one half of the imaged lines 252a through 252f (or combinations thereof).

It will be understood that the scale of the imaged lines discussed above (e.g., 252a through 252f and 240a through 240e), as well as various other features of relevant images, are presented as examples only. In other implementations, for example, a relevant image can be composed from a significantly greater number of imaged lines, each of which lines can correspondingly cover a significantly smaller portion of the object 100.

In some implementations, the machine vision system 20 can additionally (or alternatively) be configured to adapt other operations. In this regard, for example, the tool adjustment module 176 can sometimes adjust parameters of a machine vision tool based upon an identified deviation of an image from a corresponding model. For example, where a square-pixel configuration of an image is not possible (or desired), where a user prefers not to adjust the sampling rate of an image acquisition (e.g., in order to improve processing speed by use of less pixel data), or where other limitations (e.g., hardware limitations) apply, it may be useful for the tool adjustment module 176 to adjust one or more parameters of select machine vision tools rather than (or in addition to) the comparison module 170 (or other module) adjusting a sampling rate for subsequent image acquisition.

In some implementations, where an aspect ratio, linear measurement or other aspect of an image deviates from a corresponding aspect of a model, the tool adjustment module 176 can adjust tools in order to address this deviation. For example, if the tool module 178 (see FIG. 2) includes a measurement (or other) tool directed towards a particular aspect ratio of an expected image of the object 100, or to another aspect (e.g., geometrical measurement) that is distorted in the acquired image (e.g., as illustrated the example images 196 and 204 of FIGS. 5B and 6B), the tool adjustment module 176 can sometimes adjust the tool to measure (or otherwise assess) a modified aspect ratio or other image aspect. Where such an adjustment of a tool corresponds to the identified deviation between an image and a model (e.g., the reduced length and width 198 and 200 of the image 196, or the reduced length 206 and distorted aspect ratio of the image 204), this may allow the relevant tool to appropriately process the relevant image, without necessarily requiring a correction of the deviation (e.g., via operation of the post-processing module 174 or calculation of an updated sampling rate, as described above).

In some implementations, other tool adjustments may also (or alternatively) be possible. For example, in some implementations, based upon similar analysis to that outlined above, the tool adjustment module 176 can adjust a region of interest for a histogram, shape-finding or other tool. In some implementations, such adjustment (or others) can be executed in combination with, dependent on, or in a manner otherwise related to, a corresponding tool adjustment relative to a relevant aspect ratio. In some implementations, the tool adjustment module 187 can apply an adjustment factor to pixel counts of a histogram tool, in order to account for identified differences in the acquired pixels with regard to expected, optimal, or typical pixel characteristics. In some implementations, the tool adjustment module 187 can implement particular threshold values or other parameters based on a number of acquired pixels, modifications or identified deviations in an aspect ratio, and so on.

In some implementations, it may be useful to post-process an image in addition to assessing the image with tools that have been adjusted by the tool adjustment module 176. For example, a user may sometimes prefer to view representations of acquired images with square-pixel configuration (or other character of aspect ratio), even if the image itself can be appropriately analyzed by tools of the tool module 178 despite exhibiting a non-square-pixel configuration, deviated aspect ratio, or other deficiency. In such a case, the post-processing module 174 (or another module) can cause the image to be displayed to the user with a desired configuration (e.g., with square pixels, a non-distorted aspect ratio, and so on), even if the image may not necessarily be subjected to post-processing (e.g., by the post-processing module 174, as described above).

Figure 10:
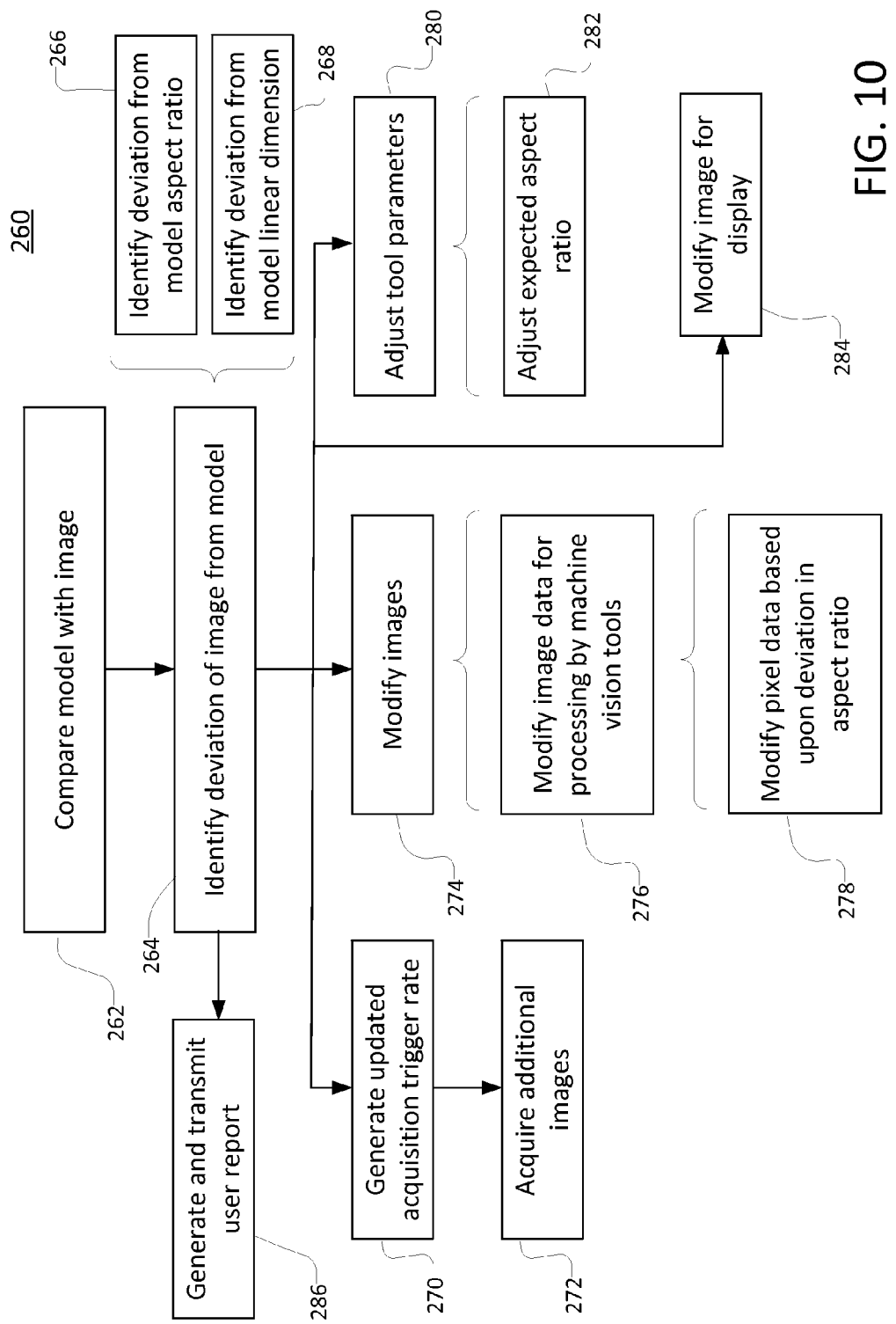
FIG. 10 is a flow chart of another method in accordance with the present disclosure.

As illustrated in FIG. 10, a method 260 can be used to implement one or more of the functions discussed above (and other functionality). As indicated at process block 262, for example, an acquired image (or images) of an object (or objects) can be compared with a model (or models) of the object (or objects). Such comparison, as also discussed above, can include comparing linear (or other) dimensions, aspect ratios, or other aspects of the relevant image and model.

As indicated at process block 264, comparing an image and a model can lead to identifying a deviation of the images from the model. As indicated at process block 266 and 268, for example, identifying a deviation of an image from a model can include identifying a deviation of an actual aspect ratio from a model aspect ratio, or a deviation of an actual linear dimension from a model linear dimension. As illustrated in FIGS. 5A through 6B, for example, comparison of an image (e.g., one of the images 196 and 204) and model (e.g., the model 190) can result in identification of a difference in length, width, or aspect ratio of the image, relative to the model.

In some implementations, as indicated at process block 270, the deviation of the image from the model, along with the movement of the virtual axis 88, can be used to generate an updated acquisition trigger rate that virtually follows the movement of the one or more objects. As indicated at process block 272, the image acquisition device and the updated acquisition trigger signal can then be used to acquire additional one or more images of the one or more objects. As illustrated in FIG. 3, for example, an updated angular interval on the virtual axis 88 (e.g., the updated angular interval 232) can be translated into an updated image acquisition trigger signal (e.g., the updated image acquisition trigger signal 234) in order to trigger image capture that is more appropriately aligned with actual movement of the relevant object (e.g., the object 100).

Figure 8B:
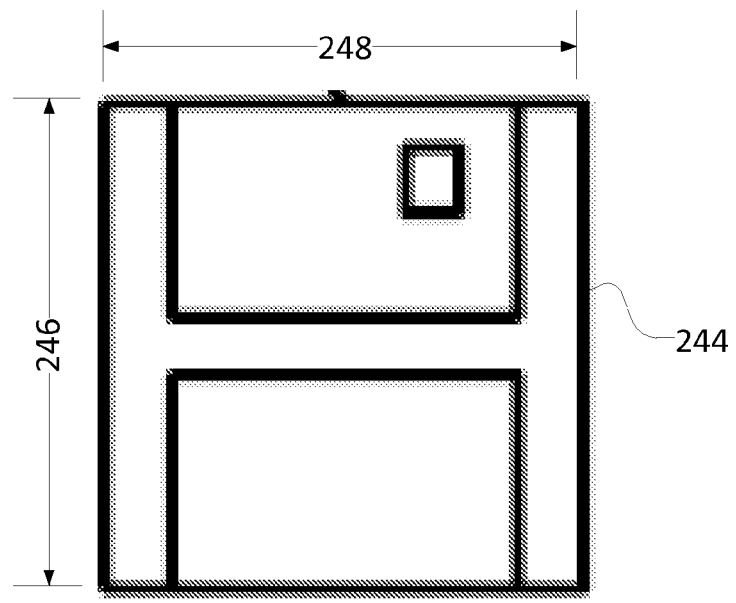
FIG. 8B is a schematic view of a modified image after the modification partially illustrated in FIG. 8A.

In some implementations, as indicated at process block 274, the relevant image can be modified based upon the identified deviation, including, as indicated at process block 276, for further processing by one or more machine vision tools. For example, as indicated at process block 278 and also illustrated in FIGS. 8A and 8B, pixel data for an image (e.g., the image 204) can be modified (e.g., added to, stretched, smoothed, and so on) based on deviations in aspect ratio (or other deviations) in order to generate an updated image 244 that is more appropriately configured (e.g., exhibits an appropriate aspect ratio) for analysis by various machine vision tools (e.g., tools of the tool module 178 of FIG. 2).

In some implementations, as indicated at process block 280, an identified deviation of an image from a model (e.g., under the process block 264) can be used to adjust parameters of a machine vision tool for the processing the relevant image. As indicated at process block 282, for example, and as also discussed above, a machine vision tool included in the tool module 178 can be modified to measure or otherwise assess an image using a target aspect ratio that has been modified based upon an identified deviation between the aspect ratios of the relevant image and model, rather than using an original (e.g., unmodified) target aspect ratio.

In some implementations, as indicated at process block 284, an image can be modified for display to a user. For example, where an acquired image does not exhibit a desired square-pixel configuration, the image can be modified under the process block 284 to exhibit a square-pixel configuration when displayed to a user. As also noted above, an image can be modified for display (e.g., under the process block 284) whether or not the image has been modified (e.g., under the process blocks 276 and 278) for analysis by a machine vision tool.

In some implementations, as indicated at process block 286, a user report can be generated and transmit for consumption (e.g., viewing) by a user. As also discussed above, for example, a user report under the process block 286 can be used to alert a user that the relevant camera may have been unexpectedly moved, that a current sampling rate for the camera may result in images that deviate from a model, or that a motion system (e.g., the conveyor 66 or other devices) are exhibiting undesirable behaviors, such as jitter or slack.

Various examples systems and methods presented above address implementations that utilize (e.g., rely upon, or adjust) the virtual axis 88, as expressly described above. It will be understood that various other implementations are possible. In some implementations, a virtual axis can be used (e.g., as generated by the virtual axis application 86) that is essentially directly driven by a relevant encoder (e.g., the encoder 36). For example, a virtual axis can be configured to essentially mirror movements registered by the encoder 36. In some implementations, a signal from the encoder 36 can be used directly to determine the timing of a trigger signal or other aspect of image acquisition, as well as to at least partly control various other operations discussed herein.

In some implementations, various operations of the method 260 (or similar methods) can be implemented without necessarily relying on a virtual axis, such as the virtual axis 88. For example, in some cases, the generation 270 of updated acquisition trigger rates, the modification 274 of various images, the adjustment 280 of tool parameters, the modification 284 of an image for display, and so on (see, e.g., FIG. 10) can be implemented without necessarily using the virtual axis 88 (or another virtual axis). In some implementations, such operations may be usefully applied in the general context of line-scan imaging devices (e.g., line-scan cameras), again, without necessarily using the virtual axis 88 (or another virtual axis).

Although the present invention has been described with reference to preferred embodiments, workers skilled in the art will recognize that changes may be made in form and detail without departing from the spirit and scope of the invention. For example, the present invention is not limited to the embodiments of smart cameras and associated devices shown herein and may be practiced with other image acquisition devices.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A vision system for triggering image acquisition of one or more objects using motion data communicated from a motion controller on a network, the motion controller coupled to a motion drive, the system comprising:
    an image acquisition device;
    an acquisition controller coupled to the image acquisition device, the acquisition controller including a network interface, the network interface operable to couple to the network;
    wherein the acquisition controller, upon receiving motion data from the motion controller, uses a virtual axis application to plan movement of a virtual axis for a motion cycle, the virtual axis allowing an acquisition trigger rate to be calculated by the acquisition controller that follows movement of the one or more objects caused by the motion drive; and
    wherein, based on the calculated acquisition trigger rate, the acquisition controller generates an acquisition trigger signal for triggering the image acquisition of the one or more objects.

2. The vision system according to claim 1, further comprising:
    a comparison module configured to:
        compare a model of the one or more objects to image data from the image acquisition of the one or more objects; and
        identify a deviation of the image data from the model;
    wherein, based upon the deviation of the image data from the model and the movement of the virtual axis, the acquisition controller calculates an updated acquisition trigger rate; and
    wherein, based on the updated acquisition trigger rate, the acquisition controller generates an updated acquisition trigger signal for triggering subsequent image acquisition of the one or more objects.

3. The vision system according to claim 2, wherein the model of the one or more objects includes one or more virtual objects.

4. The vision system according to claim 2, wherein identifying the deviation of the image data from the model includes identifying one or more of a deviation of an aspect ratio represented in the image data from a model aspect ratio, and a deviation of a linear dimension represented in the image data from a model linear dimension.

5. The vision system according to claim 4, wherein the updated acquisition trigger rate corrects for the deviation in the aspect ratio represented in the image data.

6. The vision system according to claim 2, wherein identifying the deviation of the image data from the model includes identifying, for a movement of the one or more objects that is caused by the motion drive, an effect of one or more of jitter and slack on the movement.

7. The vision system according to claim 2, further comprising:
    a reporting module configured to generate a user report based upon the deviation of the image data from the model, and to transmit the user report for review by a user.

8. The vision system according to claim 1, further comprising:
    a comparison module configured to:
        compare a model of the one or more objects to image data from the image acquisition of the one or more objects; and
        identify a deviation of the image data from the model; and a post-processing module configured to modify the image data, for further processing by one or more machine vision tools, based upon the deviation of the image data from the model.

9. The vision system according to claim 8, wherein the modifying of the image data by the post-processing module includes modifying pixel data in order to rescale an aspect ratio represented in the image data.

10. The vision system according to claim 1, further comprising:
a comparison module configured to:
compare a model of the one or more objects to image data from the image acquisition of the one or more objects; and
identify a deviation of the image data from the model; and
a tool adjustment module configured to adjust one or more parameters of one or more machine vision tools, based upon the deviation of the image data from the model.

11. The vision system according to claim 10,
wherein identifying the deviation of the image data from the model includes identifying a deviation of an aspect ratio represented in the image data from a model aspect ratio; and
wherein adjusting the one or more parameters of the one or more machine vision tools includes adjusting the one or more parameters based upon the deviation of the aspect ratio represented in the image data.

12. A vision system comprising:
an image acquisition device operable to trigger image acquisition of one or more objects using motion data communicated from a motion controller on a network, the motion controller coupled to a motion drive;
the image acquisition device being in communication with a virtual axis application and an acquisition controller, the acquisition controller being coupleable to the network;
a common time reference provided by at least one of the motion controller, an image acquisition device clock, a dedicated master clock, and the motion drive;
wherein the image acquisition device, upon receiving the motion data communicated from the motion controller, uses the virtual axis application to plan movement of a virtual axis for a motion cycle, the virtual axis operable to follow relative movement of the one or more objects caused by the motion drive; and
wherein, based on movement of the virtual axis, the image acquisition device generates an acquisition trigger signal for triggering the image acquisition of the one or more objects.

13. The vision system according to claim 12, wherein the image acquisition device compares a model of the one or more objects to image data from the image acquisition of the one or more objects in order to identify a deviation of the image data from the model;
wherein, based upon the deviation of the image data from the model and the movement of the virtual axis, the image acquisition device generates an updated acquisition trigger signal; and
wherein, based on the updated acquisition trigger rate, the image acquisition device generates an updated acquisition trigger signal for triggering subsequent image acquisition of the one or more objects.

14. The vision system according to claim 13, wherein the acquisition trigger signal triggers the image acquisition at first angular intervals of the movement of the virtual axis; and wherein the updated acquisition trigger signal triggers the subsequent image acquisition at second angular intervals of the movement of the virtual axis, the second angular intervals being at least partly different from the first angular intervals.

15. The vision system according to claim 12, wherein the image acquisition device compares a model of the one or more objects to image data from the image acquisition of the one or more objects in order to identify a deviation of the image data from the model; and
wherein the image acquisition device modifies the image data, based upon the deviation of the image data from the model, for further processing by one or more machine vision tools.

16. The vision system according to claim 12, wherein the image acquisition device compares a model of the one or more objects to image data from the image acquisition of the one or more objects in order to identify a deviation of the image data from the model; and
wherein the image acquisition device adjusts one or more parameters of one or more machine vision tools, based upon the deviation of the image data from the model, for further processing of the image data by one or more machine vision tools.

17. A method for acquiring one or more images of one or more objects, the method comprising:
providing a common time reference to an image acquisition device and a motion controller, the image acquisition device and the motion controller being in communication on a network;
the motion controller sending motion data to a motion drive;
the motion controller sending the motion data over the network to the image acquisition device;
upon receiving the motion data, the image acquisition device planning movement of a virtual axis, such that the virtual axis moves in a fixed relationship to the motion drive;
using the virtual axis, generating an image acquisition trigger rate that virtually follows movement of the one or more objects;
using the image acquisition trigger rate, generating an image acquisition trigger signal; and
using the image acquisition device and the image acquisition trigger signal, acquiring the one or more images of the one or more objects.

18. The method according to claim 17, further comprising:
comparing a model of the one or more objects to the one or more images;
identifying a deviation of the one or more images from the model;
using the deviation of the one or more images from the model and the movement of the virtual axis, generating an updated acquisition trigger rate that virtually follows the movement of the one or more objects; and
using the image acquisition device and the updated acquisition trigger signal, acquiring additional one or more images of the one or more objects.

19. The method according to claim 17, further comprising:
comparing a model of the one or more objects to the one or more images;
identifying a deviation of the one or more images from the model; and using the deviation of the one or more images from the model, modifying the one or more images for further processing by one or more machine vision tools.

20. The method according to claim 17, further comprising:
comparing a model of the one or more objects to the one or more images;
identifying a deviation of the one or more images from the model; and
using the deviation of the one or more images from the model, adjusting one or more parameters of one or more machine vision tools for processing the one or more images.

* * * * *